United States Patent
Poch

(10) Patent No.: US 7,841,189 B2
(45) Date of Patent: Nov. 30, 2010

(54) DEVICE FOR ADJUSTING THE TEMPERATURE OF A PHYSIOLOGICAL FLUID

(75) Inventor: Jaime Arbos Poch, Madrid (ES)

(73) Assignee: Laboratorios Cair Espana, S.L., Madrid (ES)

( * ) Notice: Subject to any disclaimer, the term of this patent is extended or adjusted under 35 U.S.C. 154(b) by 330 days.

(21) Appl. No.: 12/157,928

(22) Filed: Jun. 13, 2008

(65) Prior Publication Data

US 2009/0056344 A1 Mar. 5, 2009

Related U.S. Application Data

(63) Continuation of application No. PCT/ES2005/000679, filed on Dec. 15, 2005.

(51) Int. Cl.
F25B 21/02 (2006.01)

(52) U.S. Cl. .............................. 62/3.3; 62/3.7

(58) Field of Classification Search ............. 62/3.2, 62/3.3, 3.6, 3.7, 126, 157, 434, 449; 312/109, 312/111, 140
See application file for complete search history.

(56) References Cited

U.S. PATENT DOCUMENTS

| | | | |
|---|---|---|---|
| 3,399,536 A | | 9/1968 | Walz |
| 3,860,818 A * | 1/1975 | Stalder et al. ............... 250/343 |
| 4,314,967 A * | 2/1982 | Kwon et al. .................. 422/49 |
| 4,844,074 A | | 7/1989 | Kurucz |
| 5,188,286 A * | 2/1993 | Pence, IV ................... 236/1 F |
| 5,522,216 A * | 6/1996 | Park et al. ...................... 62/3.6 |
| 5,544,487 A * | 8/1996 | Attey et al. ................... 62/3.7 |
| 5,561,981 A * | 10/1996 | Quisenberry et al. .......... 62/3.7 |
| 5,653,111 A * | 8/1997 | Attey et al. ................... 62/3.7 |
| 5,704,212 A * | 1/1998 | Erler et al. ..................... 62/3.2 |
| 5,718,375 A * | 2/1998 | Gerard ................... 237/12.3 R |
| 5,761,909 A * | 6/1998 | Hughes et al. ................ 62/3.7 |
| 5,896,832 A * | 4/1999 | Aoki et al. ..................... 122/26 |
| 6,295,820 B1 * | 10/2001 | Cauchy et al. ................ 62/3.6 |
| 6,530,231 B1 * | 3/2003 | Nagy et al. ................... 62/3.2 |
| 6,619,044 B2 * | 9/2003 | Batchelor et al. ............. 62/3.3 |
| 6,628,448 B2 * | 9/2003 | Ohtsuka et al. ............. 359/240 |
| 7,131,486 B2 * | 11/2006 | Goodson et al. ........... 165/80.4 |
| 7,134,486 B2 * | 11/2006 | Santiago et al. ........ 165/104.28 |

(Continued)

FOREIGN PATENT DOCUMENTS

JP 2000093449 4/2000

*Primary Examiner*—Mohammad M Ali
(74) *Attorney, Agent, or Firm*—Klauber & Jackson LLC

(57) ABSTRACT

The invention relates to a device for adjusting the temperature of a physiological fluid. The inventive device includes: a casing (1), a first heat energy generating unit (2), a heat energy receiving unit (3) through which the fluid flows along a passage from a fluid inlet (3a) to a fluid outlet (3b) and which consists of a flat body (3d) having a first large surface (3e) which is made from a heat conductor material, and a control unit (4) for controlling at least the first generating unit (2). According to the invention, the first generating unit (2) includes first units of Peltier cells (5) and at least one first contact plate (6) which is made from a heat conductor material and which is placed in contact with a first side (5b, 8b) of the units of Peltier cells (5). In addition, the receiving unit (3) is removably installed in the first generating unit (2) such that it is in contact with the first contact plate (6).

23 Claims, 7 Drawing Sheets

U.S. PATENT DOCUMENTS

| | | | |
|---|---|---|---|
| 7,158,717 B2 * | 1/2007 | Young et al. | 392/444 |
| 7,310,953 B2 * | 12/2007 | Pham et al. | 62/3.2 |
| 2002/0085356 A1 * | 7/2002 | Ishimine et al. | 361/700 |
| 2003/0062149 A1 * | 4/2003 | Goodson et al. | 165/104.11 |
| 2003/0164231 A1 * | 9/2003 | Goodson et al. | 165/104.11 |
| 2003/0188538 A1 * | 10/2003 | Chu et al. | 62/3.2 |
| 2004/0079089 A1 | 4/2004 | Wallach | |
| 2004/0089442 A1 * | 5/2004 | Goodson et al. | 165/104.11 |
| 2005/0098299 A1 * | 5/2005 | Goodson et al. | 165/80.3 |
| 2005/0205241 A1 * | 9/2005 | Goodson et al. | 165/80.4 |

* cited by examiner

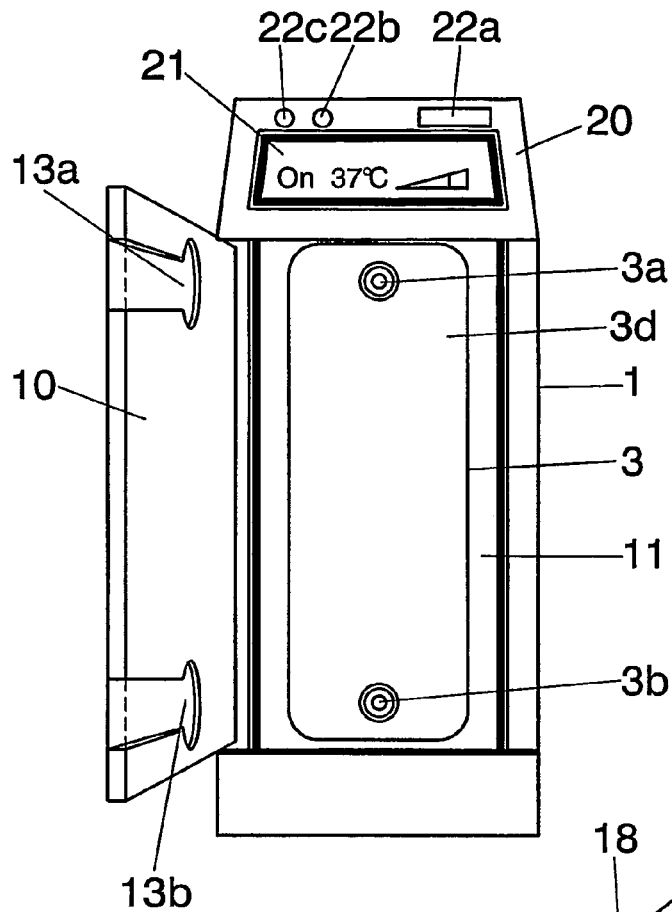
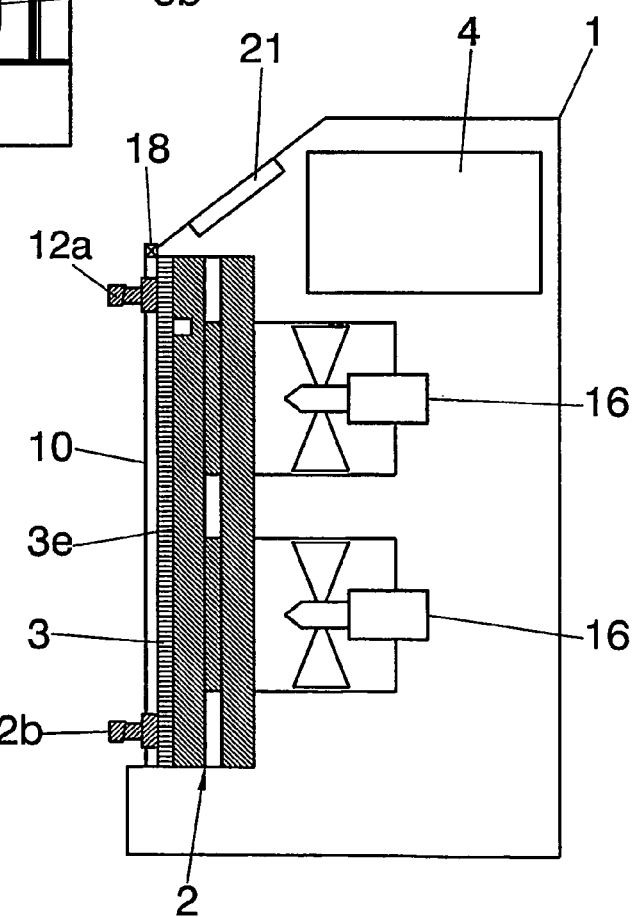

DEVICE FOR ADJUSTING THE TEMPERATURE OF A PHYSIOLOGICAL FLUID

RELATED APPLICATION

The present application is a Continuation of co-pending PCT Application No. PCT/ES2005/000679, filed Dec. 15, 2005. Applicants claim the benefits of 35 U.S.C. §120 as to the PCT application, and the entire disclosure of said application is incorporated herein by reference in its entirety.

TECHNICAL FIELD OF THE INVENTION

The present invention comes within the technical field of devices intended for adjusting the temperature of physiological fluids prior to being administered to patients.

BACKGROUND OF THE INVENTION

Nowadays there are a great many medical and veterinary treatments in which fluids are infused into the circulatory system of patients or animals. Very frequently, and especially when the fluids to be infused have previously been kept under refrigeration, a difference occurs between the temperature of the fluid to infuse and the body temperature of the individual to treat, and this difference is liable to disturb the thermal system of the individual and, in extreme cases, it can produce a thermal shock with sometimes lethal consequences.

So, on many occasions, as with hemorrhages occurring during operations or as a result of accidents, fluids such as blood conserves, cellular preparations or serum have to be infused into the individual very quickly. Bearing in mind that, for example, blood conserves are stored at temperatures of around 4° C., in order to avoid the negative consequences of the difference between the temperature of a blood conserve and the body temperature of the individual to whom the blood has to be administered, the conserves have to be warmed up to a temperature close to the body temperature of the individual. This, under circumstances in which an urgent and rapid administration is needed, requires a fast and efficient warming of the blood to the necessary temperature.

Moreover, in certain types of treatments and surgical operations, such as dialysis or heart surgery, extracorporeal blood circulation needs to be established in which the blood recirculated to the individual has to be kept at a constant temperature as close as possible to body temperature.

There exist devices that permit warming of physiological fluids, basically consisting of a heating apparatus which heats water to a predetermined temperature and circulates the water through a closed heat exchange device through which flows the liquid to be warmed, it collects the water from the outlet from the exchange device, reheats the water and recirculates it to the exchange device. Another type of heat exchange device for warming up physiological fluids is described, for example, in German patent DE-DE-C-827702, in European patent application EP-A-0463837 and in Spanish patent application P9700855. This type of device includes an exterior tube for the circulation of a heating fluid with a space that houses an interior tube through which the physiological fluid flows. This space is divided into a first channel through which warm fluid enters until it encounters the recirculation of heating fluid at the opposite end of the exterior tube from whose space the heating fluid enters into the second channel and returns to the heating apparatus.

Spanish patent application ES-A-2200609 describes a heat exchange device between a heating fluid and a fluid to be heated, particularly a physiological fluid, having a simple and economical structure, with a casing divided into a first compartment and a second compartment by a partition and linked by a communication passage, and with an exchange element provided in the first compartment. The heating fluid inlet discharges into the first compartment and the outlet of the heating fluid links with the second compartment, the inlet and outlet being opposite to the communication passage and provided with connector elements grouped into a dual connector for connection to complementary elements of a system for heating and recirculation of heating fluid.

Although the systems of the state of the art described above have been used in the heating of physiological fluids, they present a series of drawbacks. So, the heating of the physiological fluid has to be done via another fluid, water, which has to transfer its heat energy to the physiological fluid with the consequent energy losses and the impossibility of making any fine and immediate adjustment to the temperature at which the physiological fluid has to be infused. Also, these systems need a water circuit which, on the one hand, requires space and is relatively costly to manufacture, and, on the other, presents problems of sterility since, via micropores in joints and tubes, the water can possibly become contaminated with biological agents present in the environment.

It was therefore desirable to have a device that would permit the said drawbacks of the systems in the state of the art to be overcome.

SUMMARY OF THE INVENTION

The aim of the present invention is to overcome the drawbacks of the state of the art by means of a device for adjusting the temperature of a physiological fluid which includes a casing, at least one first heat energy generating unit, a heat energy receiving unit through which the fluid flows along a channel from a fluid inlet to a fluid outlet and which consists of a flat body having a first large surface which is made from a heat conductor material, a control unit for controlling at least the first heat energy generating unit, and which includes a microprocessor, in which device the first heat energy generating unit includes a plurality of first units of Peltier cells and at least one first contact plate made of a heat conductor material placed in contact with a first side of the units of Peltier cells, and the receiving unit is removably installed in the first heat energy generating unit such that it is in contact with the first contact plate.

Given that Peltier cells generate heat on one of their sides ("cold side") and cold on the other ("hot side"), depending on the polarity of the direct current supplied, in the device of this patent application the first heat energy generating unit can, by choosing a first polarity of the electric current supplied to those cells, be designed so that it is a heating unit, in which case the first side of the first plurality of units of Peltier cells that is in contact with the first contact plate is the hot side of the first plurality of units of Peltier cells. Moreover, by choosing an opposite polarity of the electric current, the first heat energy generating unit can be a cooling unit, in which case the first side of the first plurality of units of Peltier cells that is in contact with the first contact plate is the cold side of the first plurality of units of Peltier cells.

Accordingly, with a substantially equal basic structure, the device of the present invention can, according to the polarity of the electric current with which the Peltier cells are fed, be designed for just heating (keeping the same polarity at all times) or just for cooling (keeping the same polarity at all times), or it can be designed for being able to perform both functions (via means which permit the polarity incorporated into the control unit to be changed).

The device preferably includes at least one first temperature sensor which detects the temperature in the first contact plate and which is connected to the control unit. In turn, the, microprocessor is programmed for supplying electrical energy to said first units of Peltier cells depending on the difference between a pre-established nominal temperature and the temperature detected by the temperature sensor. Likewise, and according to a preferred embodiment of the invention, the microprocessor can be programmed to control the polarity of the electric current supplied to the units of Peltier cells in order to warm up or cool down the first side of the units of Peltier cells.

The Peltier cells and the arrangement of the heat conductor elements making up the device of the present invention permit rapid heating and/or cooling of the physiological fluid flowing through the receiving unit. So, the heat generation response to the application of electric currents in the Peltier cells is very fast and they therefore transmit the heat energy to the heat conductor elements, in other words, to the contact plate or plates, and from there to the receiving unit, in a manner that is practically immediate, with which the device does not require any prolonged preheating. Moreover, the deviations in a nominal temperature can be rapidly corrected by supplying more or less electrical energy to the Peltier cells.

In the embodiment with a single heat energy generating unit, the casing is designed in such a way that it includes an access hatch to the interior of the casing facing the first heat energy generating unit. Between the hatch and the first generating unit is a space in which is housed the removable receiving unit, immobilized by means that are conventional in themselves, such as for example clipping flanges. The fluid inlet for the receiving unit includes a first hollow connector while its fluid outlet includes a second hollow connector. These hollow connectors, to which are connected the lines of the incoming and outgoing physiological fluid to and from the heat energy receiving unit, project from the surface of the receiving unit opposite to the first large surface which is in contact with the contact plate. The hatch in turn presents a first passage hole for the first connector and a second passage hole for the second connector.

In another embodiment of the device with a single heat energy generating unit, the casing includes a flat compartment for housing the receiving unit, said compartment including an access opening for the insertion of the receiving unit, and at least one wall of said compartment being formed by the first contact plate. In this embodiment the fluid inlet and outlet for the receiving unit are arranged on the same side of the receiving unit such that, when the receiving unit is inserted in the compartment, the fluid inlet and outlet are accessible via the access mouth. The receiving unit thus remains inserted into that compartment in the manner of a "cartridge".

The device described by the present invention can also include a second heat energy generating unit comprising a plurality of second units of Peltier cells and at least one second contact plate made of a heat conductor material placed in contact with a first side of the units of Peltier cells. In this first embodiment, the control unit also controls the second generating unit, and the receiving unit includes a second large surface made of a heat conductor material, opposite to the first large surface, in such a way that it is arranged so that its large surfaces are in contact with the first and second contact plates. In this way, the receiving unit is inserted removably in the manner of a cartridge between the first and second heat energy generating unit.

Analogously with the case of the first generating unit, the second heat energy generating unit can be designed for just heating, for just cooling or for heating and cooling. So, when the second heat energy generating unit is a heating unit, the first side of the second plurality of units of Peltier cells that is in contact with the second contact plate is the hot side of the second plurality of units of Peltier cells, while when the second heat energy generating unit is a cooling unit, the first side of second plurality of units of Peltier cells that is in contact with the second contact plate is the cold side of the second plurality of units of Peltier cells.

In this embodiment of the device with two heat energy generating units, the control unit can be designed to supply electric current in such a way that the first sides of the plurality of first units of Peltier cells and the plurality of second units of Peltier cells both operate as hot sides or as cold sides. Likewise, the device according to this embodiment can be designed so that the first side of one of the pluralities of units of Peltier cells operates as a cold side and the other as a hot side, in which case when one of these pluralities of units of Peltier cells is functioning, the other is disconnected.

In the embodiment described in the preceding paragraphs, the device preferably includes a second temperature sensor for detecting the temperature in said second contact plate and which is connected to the control unit. In this case, the microprocessor is also programmed for supplying electric current to the second units of Peltier cells depending on the difference between the pre-established nominal temperature and the temperature detected by the temperature sensor. According to a preferred embodiment of the invention, the microprocessor can be programmed for controlling the polarity of the electric current supplied to the first and second units of Peltier cells in order to heat up or cool down the respective first sides of the units of Peltier cells.

In the embodiment of the device with two heat energy generating units, the casing can include a flat compartment defined between the first and the second contact plate for housing the receiving unit. In turn, the compartment includes an access opening for insertion of the receiving unit. Also in this embodiment, the fluid inlet and outlet of the receiving unit are arranged on the same side of the receiving unit such that, when the receiving unit is inserted in the compartment, the fluid inlet and outlet are accessible via the access mouth. The receiving unit thus remains inserted into that compartment in the manner of a "cartridge".

Preferably, not just the large surfaces of the heat energy receiving unit but also the entire flat body of this unit are manufactured from a heat conductor material. A particularly suitable material is aluminum since on the one hand it is a good heat conductor which heats up and cools down rapidly, and on the other it is an economical material that can be stamped out and machined easily. These last characteristics are relevant in view of the fact that, in hospital use, the receiving unit will be a consumable item that is going to be disposed of after use.

In accordance with that stated above, the heat energy receiving unit includes a flat body inside which the physiological fluid flows from the inlet to the outlet. This passage preferably consists of a coil between the inlet and outlet of the physiological fluid. This permits a particularly efficient transfer of the heat energy to the physiological fluid.

The large surface or surfaces of the flat body of the receiving unit are preferably flat, as is the contact surface for each contact plate in such a way that a contact surface is established with the respective large surface of the receiving unit. This facilitates an efficient transfer of heat energy to the receiving unit, in addition to the fact that, when the contact surface is in contact with a hot side of the units of Peltier cells, this helps to dissipate the heat generated in that hot side.

The contact plates made of heat conductor material, such as aluminum for example, are preferably solid plates which not only permit proper transfer of the heat energy evolved by the units of Peltier cells but also proper dissipation of the heat energy. This is especially advisable in view of the known sensitivity of Peltier cells to overheating due to the accumulation of heat on their hot side.

BRIEF DESCRIPTION OF THE FIGURES

Described below are some embodiments of the device of the present invention and of its elements on the basis of certain drawings forming an integral part of this present descriptive specification. In these drawings FIG. 1 is a schematic view in front elevation of the device according to a first embodiment of the invention;

FIG. 2 is a schematic view in lateral section of the device shown in FIG. 1, with a heat energy generating unit according to a first embodiment;

Figure 3:
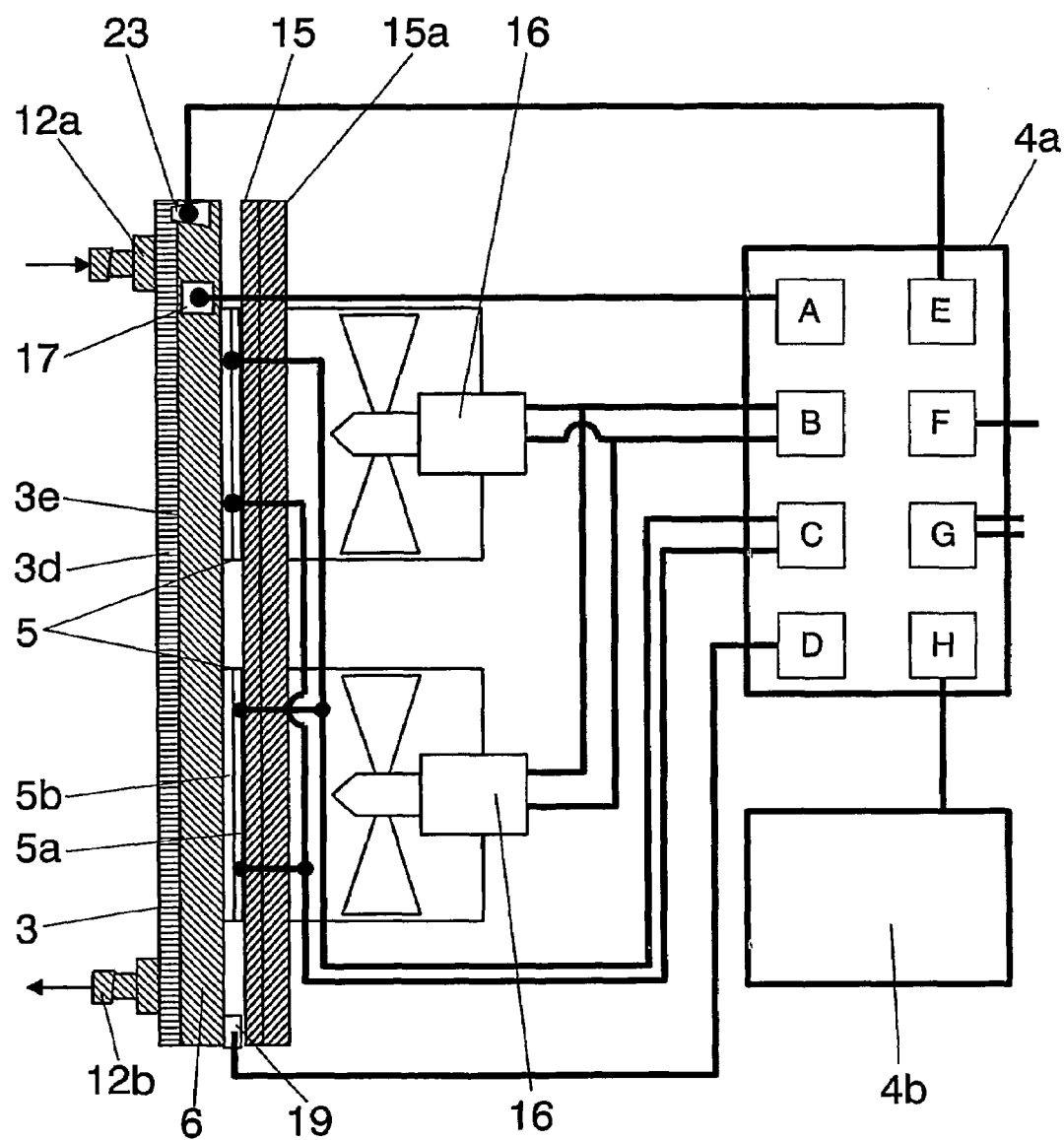
FIG. 3 is a more detailed schematic view of the heat energy generating unit shown in FIG. 2.

The references appearing in these figures denote the following elements:
1 casing
2 first heat energy generating unit
3 heat energy receiving unit
3a fluid inlet
3b fluid outlet
3c channel
3d flat body
3e first large surface made of heat conductor material
3f second large surface made of heat conductor material
4 control unit
4a connection card
4b microprocessor
5 first units of Peltier cells
5a first side of the first units of Peltier cells
5b second side of the first units of Peltier cells
6 first contact plate made of heat conductor material
6a extensions of the first contact plate
7 second heat energy generating unit
8 second units of Peltier cells
8a first side of the second units of Peltier cells
8b second side of the second units of Peltier cells
8c passage openings in the second contact plate
9 second contact plate made of heat conductor material
9a extensions of the second contact plate
10 access hatch to the interior of the casing
11 space defined between the hatch and said first generating unit
12a first hollow connector,
12b second hollow connector,
13a primer passage opening for the first connector
13b second passage opening for the second connector
14 compartment for housing the receiving unit
14a access opening to the compartment
15 dissipater
15a axial ribs
15b transverse ribs
15c second dissipater
16 fan
17 temperature sensor
17a second temperature sensor
18 hatch sensor
19 safety temperature sensor
20 control panel
21 indictor screen
22a connection switch
22b control for adjusting the temperature of the physiological fluid
22c volume control for the acoustic alarm
23 presence sensor of the receiving unit
24 network filter
25 first power supply source
26 second power supply source
A Connection of the temperature sensor to the connection card
B Connection of the fans to the connection card
C Connection of the units of Peltier cells to the connection card
D Connection of the safety temperature sensor to the connection card
E Connection of the presence sensor of the receiving unit to the connection card
F Connection of the screen and to the control panel of the connection card
G Connection of the electrical power supply to the connection card
H Connection to the microprocessor

DETAILED DESCRIPTION OF THE INVENTION

FIGS. 1 to 6 schematically illustrate a first embodiment of the device according to the present invention.

As can be seen in FIGS. 1 and 2, in this first embodiment the device includes a casing 1 provided with an access hatch 10 to the interior of the casing 1. When it is closed, the hatch 10 remains facing a first heat energy generating unit 2, such that defined between the hatch 10 and the first generating unit 2 is a space 11 in which is housed the removable receiving unit 3. Also provided in the front side part is a sensor 18 which detects whether the hatch 10 is open or closed.

The fluid inlet 3a of the receiving unit 3 includes a first hollow connector 12a that can be coupled to a line (not shown in the figures) via which the physiological fluid enters, while the fluid outlet 3b of the receiving unit 3 includes a second hollow connector 12b that can be coupled to an outlet line (not shown in the figures) towards the patient. The connectors 12a, 12b project from the surface of the receiving unit 3 opposite to its first large surface 3e.

The hatch 10 includes a first passage opening 13a for the first connector 12a and a second passage opening 13b for the second connector 12b. The passage openings 13a, 13b are extended laterally towards the free edge of the hatch 10 forming separate recesses. The purpose of these recesses is to leave a space for the inlet and outlet lines when these are connected to the respective connectors 12a, 12b. In this way, the receiving unit 3 can be coupled in the space 11 with the lines already connected and the hatch 10 can be closed.

Located in the upper front part of the casing 1 is a control panel 20 and an indicator screen 21. The control panel includes a connection switch 22a for switching the device on/off, a control 22b for adjusting the temperature of the physiological fluid being infused, and a control 22c for adjusting the volume of an acoustic warning alarm. In turn, the indicator screen 21, which can for example be an LCD conventional in itself, is suitable for indicating the adjusted temperature, the on/off status of the device and an optical alarm, coupled to the acoustic alarm, which is activated in the event of malfunctioning of the device. Evidently, the indicator screen can also be used for showing other information, such as the volume of the acoustic alarm that has been adjusted, or an indication of the correct insertion of the receiving unit, the status of the hatch (open/closed), etc.

Provided in the interior of the casing 1 and specifically behind the generating unit 2 are some fans 16 intended to dissipate the heat energy evolved by the generating unit 2 on the opposite side to the one that is in contact with the receiving unit 3.

Also to be found in the interior of the casing 1 is the control unit 4 by which the various functions of the device are controlled. The connections between the control unit and the various elements are not shown in these figures but can instead be seen in FIGS. 3 and 6 to which reference will be made further below.

FIG. 3 shows that the heat energy generating unit 2 includes two units of Peltier cells 5 and a first contact plate 6 made of a heat conductor material, such as aluminum for example, placed in contact with a second side 5b of the units of Peltier cells 5 which are connected to the connection card 4a by connection C. On the opposite side 5a of the units of Peltier cells 5 is a dissipater plate 15 provided in its rear part with axial ribs 15a. In this way, the units of Peltier cells 5 are arranged "sandwich" fashion between the contact plate 6 and the dissipater plate 15.

The upper front part of the contact plate 6 includes a presence sensor 23 which detects when the receiving unit 3 is coupled to the device such that its first large surface 3e backs onto the surface of the contact plate 6. The sensor 23 is connected to the card 4a by the connection E.

Likewise, the upper part of the contact plate 6 contains a temperature sensor 17 which detects the real temperature of the contact plate 6, and which is connected to the card 4a by the connection A.

Provided in the lower part of the contact plate 6 is a safety temperature sensor 19 which includes a microswitch which, when the temperature of the contact plate 6 exceeds a predetermined maximum (or minimum) temperature, automatically disconnects the electrical power supply to the units of Peltier cells 5, for which the sensor 19 is connected to the card 4a by the connection D.

The card also comprises separate connections B, C for the two fans 16, a connection F for the indicator screen and for the control panel, a connection G for the electrical supply, and a connection H for connection with a microprocessor 4b in which the functions of the device are programmed.

Figure 4:
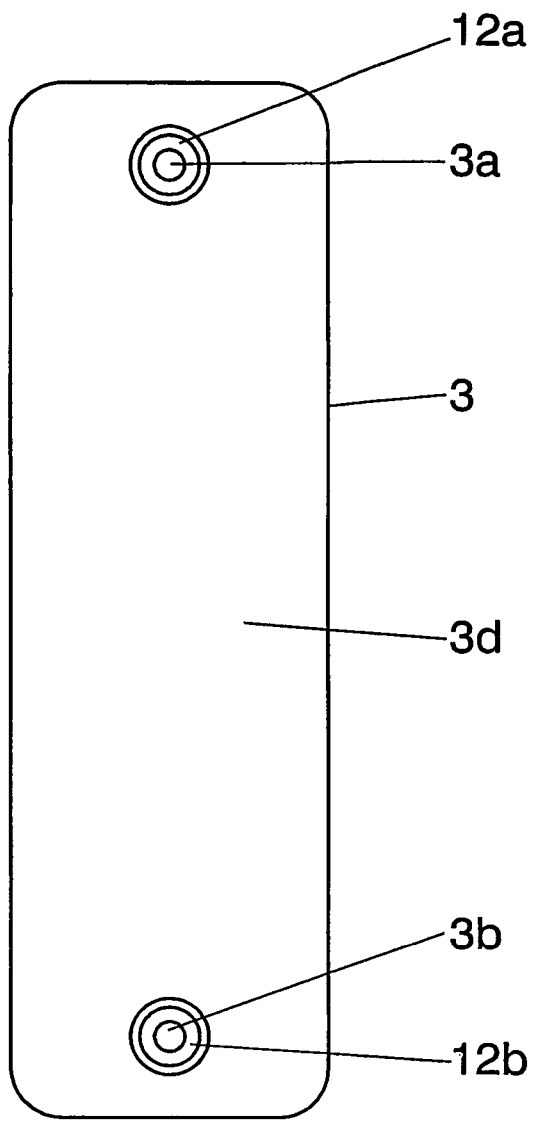
FIG. 4 is a schematic view in front plan of the receiving unit shown in FIGS. 1 to 3.
Figure 5:
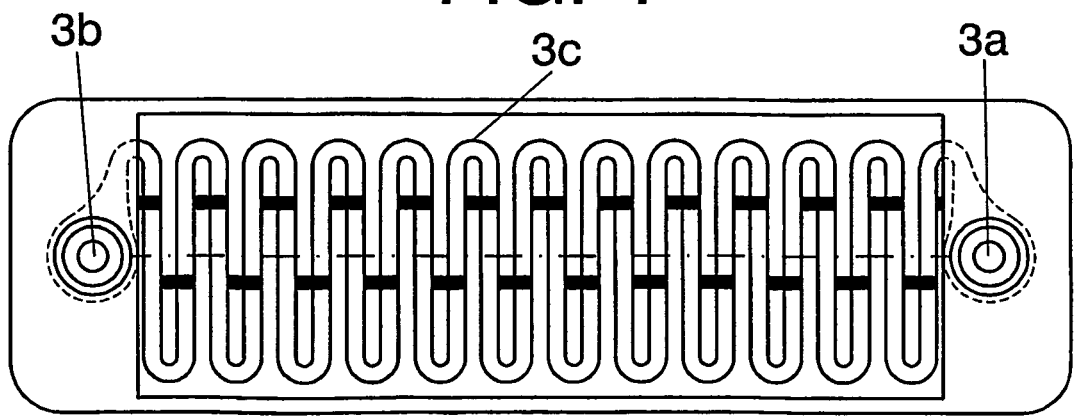
FIG. 5 is a schematic view in partially sectioned front plan of the receiving unit shown in FIG. 4.

FIGS. 4 and 5 show that the receiving unit includes a flat body 3d inside which is an interior channel 3c in the form of a coil through which flows the physiological fluid from the fluid inlet 3a to the outlet 3b. The shape of the coil of the channel 3c permits a very efficient interchange with the heat conductor material of the receiving unit 3.

Figure 6:
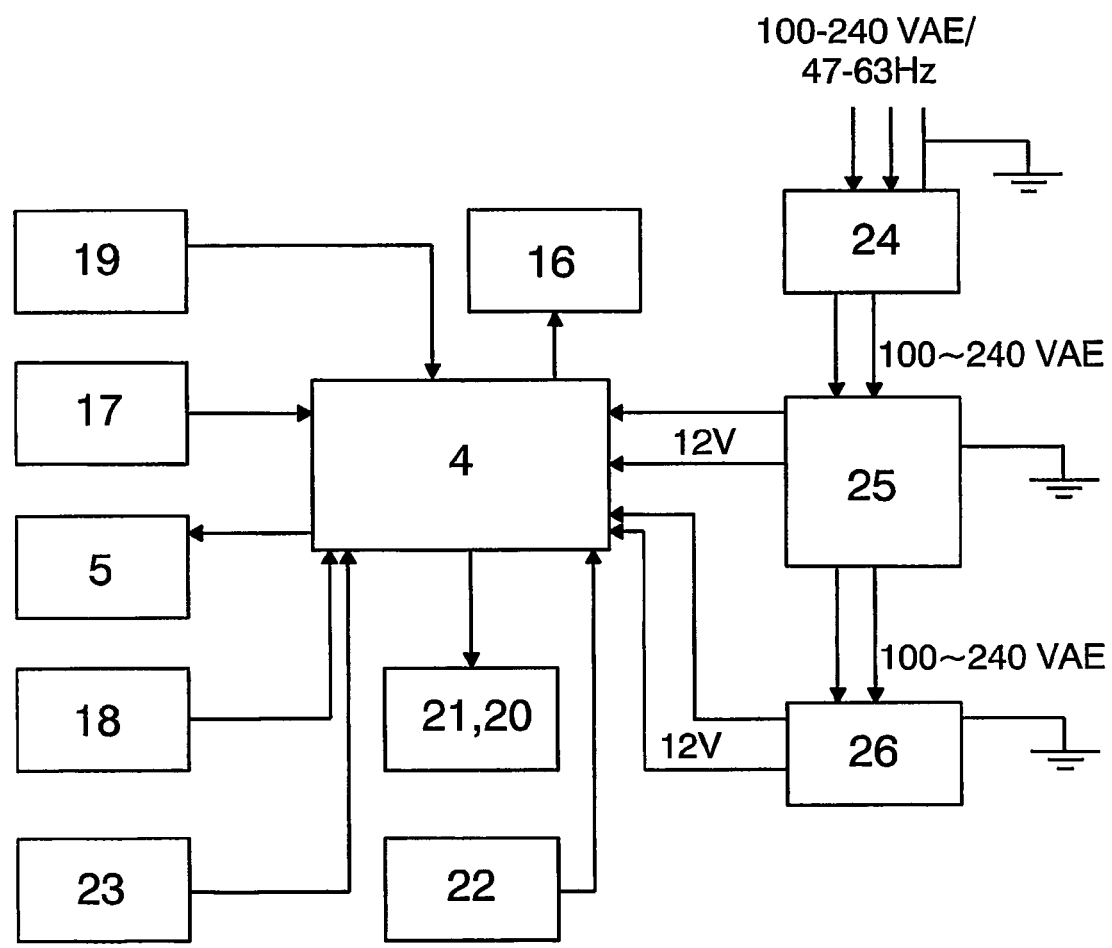
FIG. 6 is a schematic block diagram showing an example of an interconnection of the elements that can form part of the device.
Figure 7:
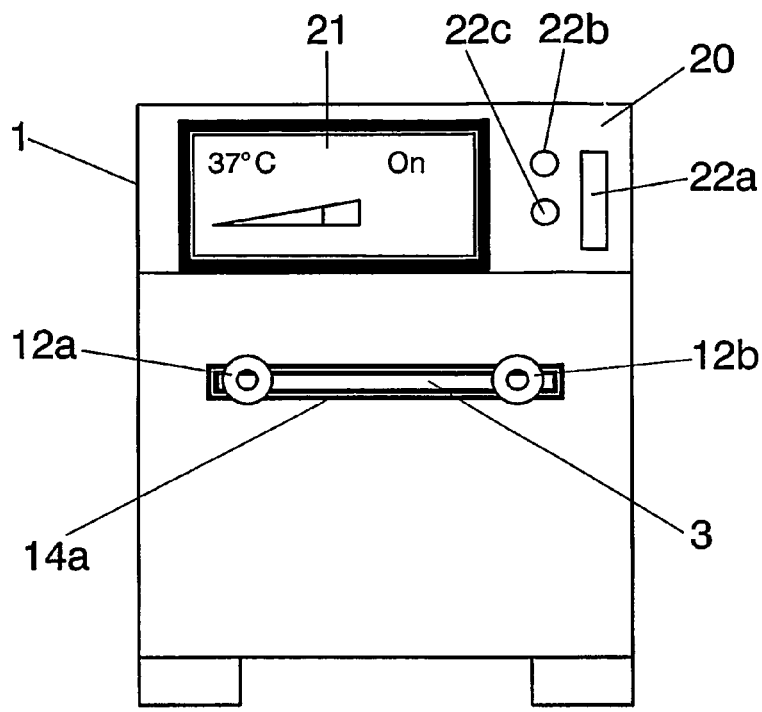
FIG. 7 is a schematic view in front elevation of the device according to a second embodiment of the invention, with a heat energy generating unit according to a second embodiment.

Shown in FIG. 6 in schematic form is the connection of several elements of the device to the control unit 4. So, in the embodiment shown in FIG. 6, the control unit 4 receives electric current from the electrical network via a network filter 24 to which are connected two power supply sources 25, 26 which transform the network electric current of 100 or 240 V into a working direct current of 12 V. The control unit 4 feeds the working current to the units of Peltier cells 5, to the fans 16, to the presence sensor 23 and to the indicator screen 21. The control unit is in turn connected to the safety temperature sensor 19, to the temperature sensor 17, to the sensor for the hatch 17 and to the control panel 20.

In the embodiment shown in FIGS. 1 to 6, the device can function in a heating mode and in a cooling mode of the physiological fluid. After switching on the device by operating the switch 22a, for functioning in heating mode first the control panel 20 is adjusted with the temperature control 22b to the desired temperature to which it is wished to heat the fluid. When the presence sensor 23 and the sensor for the hatch 18 have respectively detected that the receiving unit 3 is present and the hatch 10 is closed, the control unit 4 emits the corresponding signal to the indicator screen 21 which therefore displays the adjusted temperature. Simultaneously, the control unit 4 transmits electric current to the units of Peltier cells 5 with a polarity such that their second sides 5b operate as hot sides and their first sides 5a as cold sides, in such a way that the hot sides 5b start to warm up the contact plate 6 and thereby the physiological fluid to be found in the receiving unit 3. Likewise, the control unit 4 supplies electric current to the fans 16 so that the action of the fans 16 can extract the cold air generated in the cold sides of the units of Peltier cells 5 and transmitted to the dissipater plate 15.

When the temperature sensor 17 has detected that the contact plate 6 has reached its working temperature, the control unit 4 emits a signal to the indicator screen so that it can show that the device is ready for starting the infusion of the physiological fluid at the pre-established temperature. When the physiological fluid flows through the passage 3c of the receiving unit 3, the temperature sensor 17 detects the variations of temperature in the contact plate 6 and transmits the corresponding signals to the control unit 4 which, depending on the deviation in the temperature that has been detected by the sensor 17 of the predetermined temperature, provides more or less electrical energy to the units of Peltier cells 5. In this way, the temperature of the physiological fluid being infused into the patient can be kept stable.

In the cooling mode of the device, the functioning of the elements described above is analogous to that done in its heating mode. In this case, the temperature signal received by the temperature sensor 17 in the control unit 4 causes the latter to supply electric current to the units of Peltier cells 5 with a polarity such that current is transmitted to the units of Peltier cells 5 with a polarity such that their second sides 5b operate as cold sides and their first sides 5a as hot sides, so that the cold sides 5b cool down the contact plate 6 and thereby the physiological fluid to be found in the receiving unit 3.

The microprocessor 4b of the control unit 4 can also be programmed in such a way that, depending on the magnitude of each deviation produced, via the control of the polarity of the electric current supplied to the units of Peltier cells 5, the second sides 5*b* operate as cold or hot sides depending on whether it is necessary to increase or reduce the real temperature, thus being able to achieve a very rapid correction to deviations in real temperature from the predetermined nominal temperature.

Moreover, when the safety temperature sensor 19 detects an excessive deviation in the real temperature compared to the nominal temperature, the safety switch automatically disconnects the electrical power to the units of Peltier cells 5, so that the control unit 4 emits a signal that triggers the visual alarm and/or the acoustic alarm (not shown in the figures) of the device.

FIGS. 7 to 13 show other embodiments of the device of the present invention which have in common the fact that, in addition to first heat energy generating unit 2, they also include a second heat energy generating unit 7, arranged in such a way that the two together form a compartment 14 into which is inserted the heat energy receiving unit 3, in the manner of a cartridge, via an access opening 14*a* in the front of the casing 1. In these embodiments, the second heat energy generating unit 7 includes two second units of Peltier cells 8, a second contact plate 9, also made of a heat conductor material such as aluminum for example, placed in contact with a second side 8*b* of the units of Peltier cells 8, and a second dissipater plate 15*c* arranged on the first side 8*a* of the units of Peltier cells 8. Also provided behind the second dissipater place 15*c* are two fans 16 intended to extract the heat energy evolved by those plates 15*c*.

The receiving unit 3 in turn includes a second large surface 3*f* made of a heat conductor material, opposed to the first large surface 3*e*, and is arranged removably and in contact with the first and second contact plates 6, 9. In the embodiment shown in FIGS. 7 to 13, the connectors 12*a*, 12*b* for the fluid inlet and outlet of the receiving unit 3 are arranged on the same side of the receiving unit 3, so that, when the receiving unit 3 is inserted in the compartment 1, these connectors 12*a*, 12*b* are accessible via the access opening 14*a*.

The second generating unit 7 includes a second temperature sensor 17*a* arranged in the second contact plate 9 which, in addition to the first temperature sensor 17, measures the temperature of that second contact plate 9. The control unit 4 also controls the second generating unit 7, in a way analogous to how it controls the first generating unit 2 and in coordination with the control of the first generating unit 2.

Analogously with the case of the first generating unit 2, the second heat energy generating unit 7 can be designed to operate just in heating mode, just in cooling mode, or in both functioning modes, for which the microprocessor 4*b* of the control unit 4 has to be programmed such that the electrical current supplied to the second set of units of Peltier cells 8 has the necessary polarity for the corresponding functioning mode. In this way, when the second generating unit 7 operates as a heating unit, the second side 8*b* of the second units of Peltier cells 8 that are in contact with the second contact plate 9 is the hot side of the units of Peltier cells 8, while when the second generating unit 8 operates in cooling mode, the second side 8*b* of the second units of Peltier cells 8 that are in contact with the second contact plate 9 is the cold side of the units of Peltier cells 8. In these embodiments, provision can be made so that the second generating unit 7 always operates in the same heating or cooling mode as the first generating unit, or the second generating unit 7 operates in a mode opposite to that of the first generating unit 2, in which case the two units 2,7 do not function at the same time but instead one of them produces the heating and is switched off when the real temperature measured by the temperature sensors 17, 17*a* exceeds the predetermined temperature, while the other produces cooling and is switched off when the real temperature measured by the temperature sensors 17, 17*a* remains below the predetermined temperature.

Figure 8:
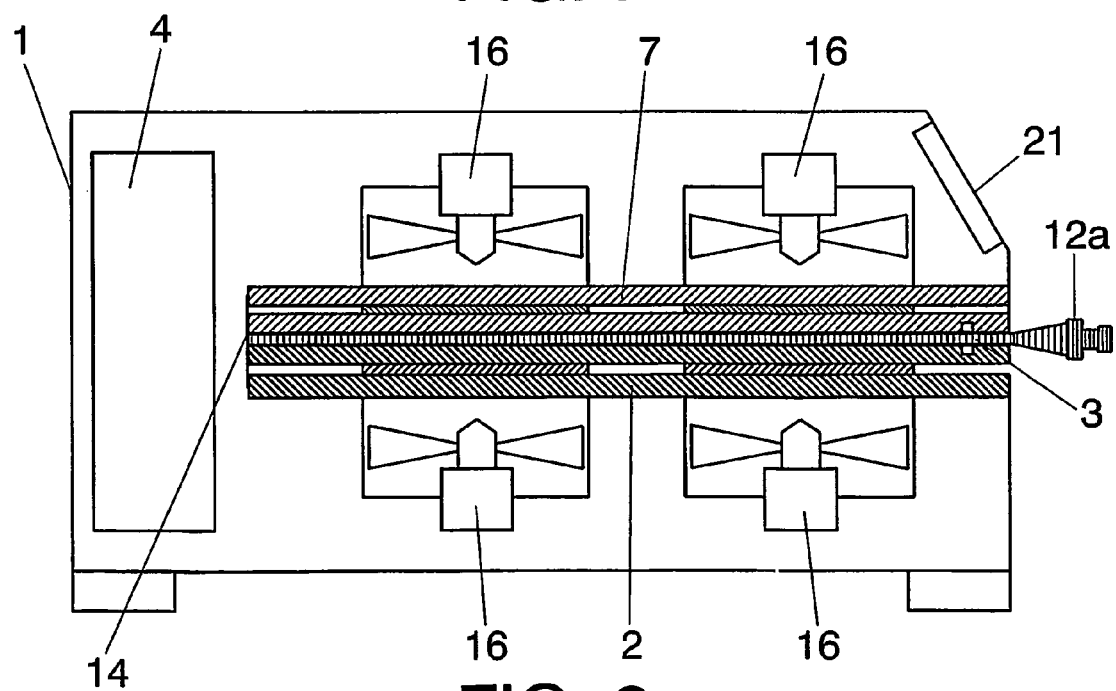
FIG. 8 is a schematic view in lateral section of the device shown in FIG. 7.
Figure 9:
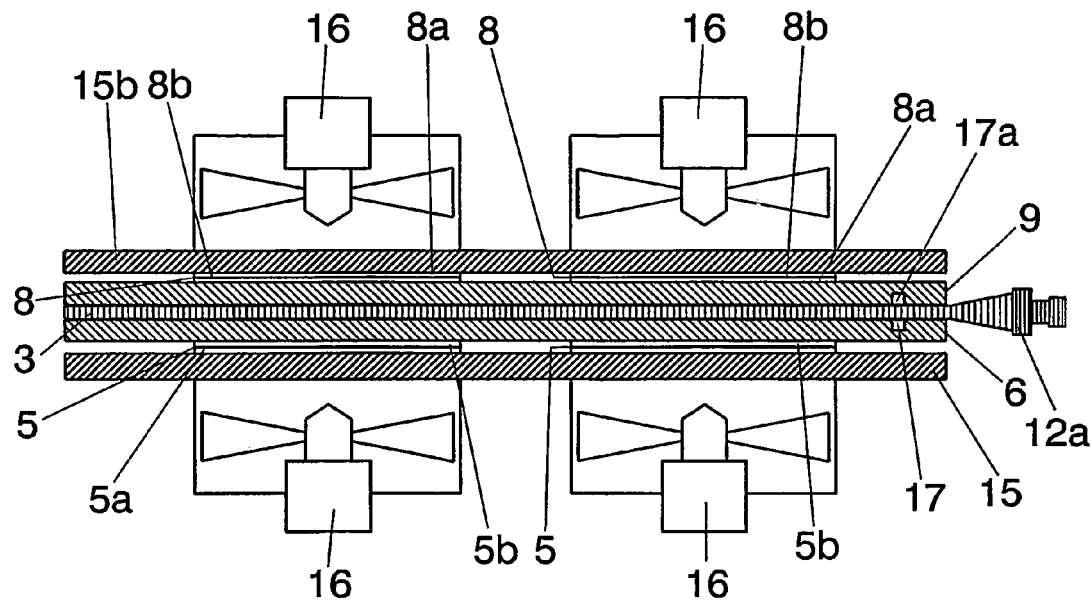
FIG. 9 is a more detailed schematic view of the heat energy generating unit shown in FIG. 8.
Figure 10:
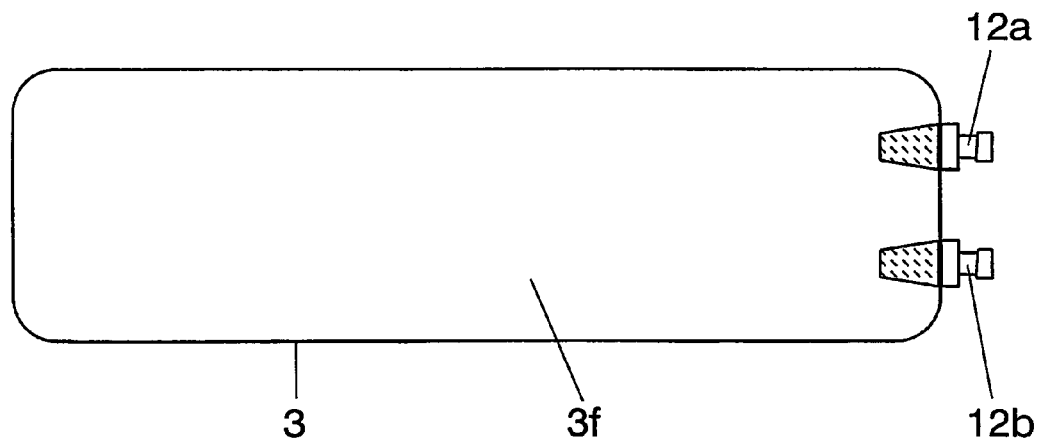
FIG. 10 is a schematic view in lower plan of the receiving unit according shown in FIGS. 6 to 9.
Figure 11:
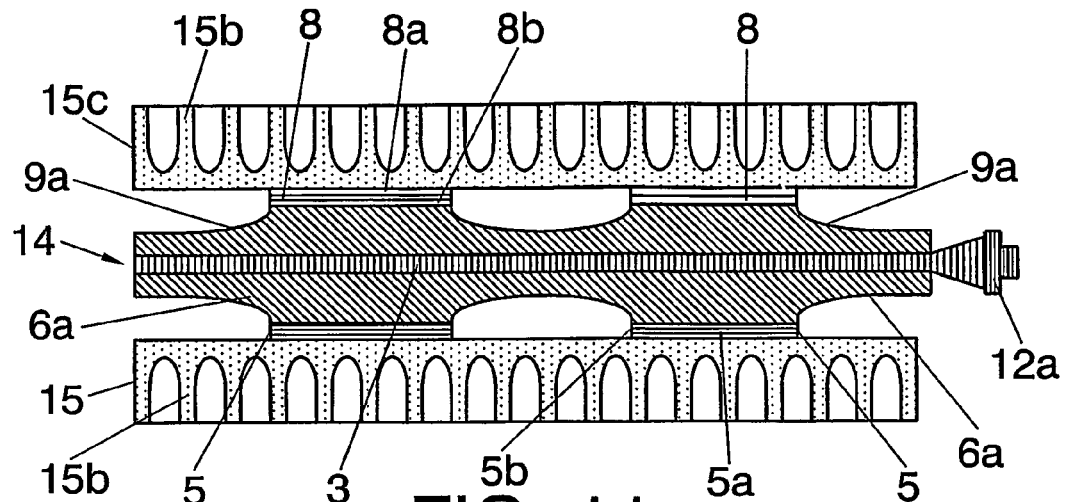
FIG. 11 is a more detailed schematic view of the heat energy generating unit according to a third embodiment.
Figure 12:
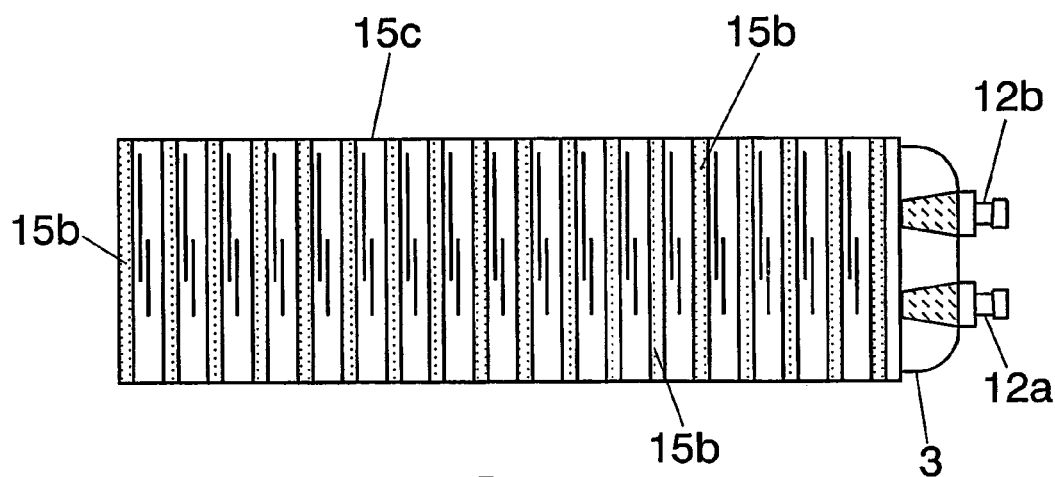
FIG. 12 is a view in upper plan of the generating unit shown in FIG. 11.
Figure 13:
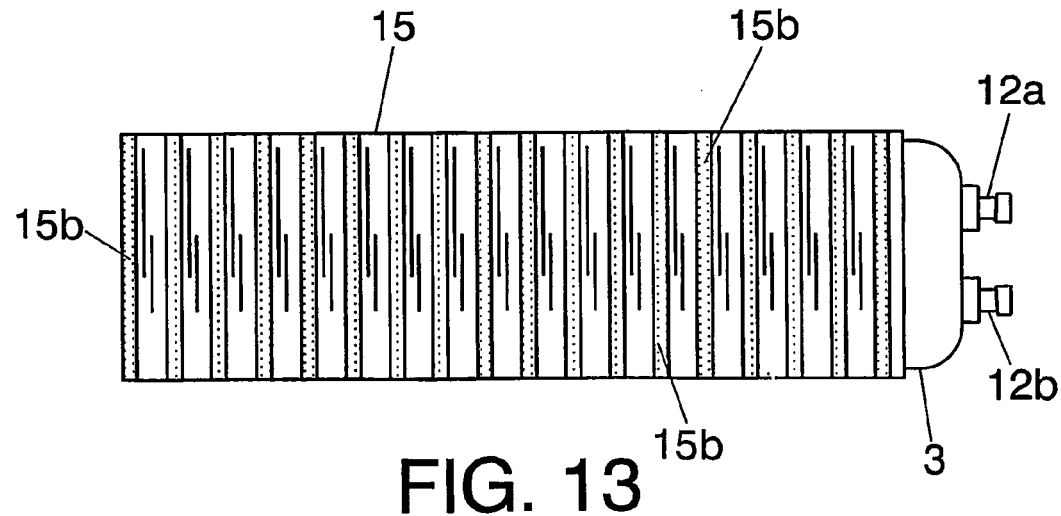
FIG. 13 is a view in lower plan of the generating unit shown in FIG. 11.

With regard to the embodiments of the device with two heat energy generating units 2,7 shown in FIGS. 7 to 13, it can be seen that FIGS. 8 and 9 show an embodiment in which the configuration of those units 2,7 is basically analogous to the first generating unit shown in FIGS. 2 and 3, while the generating units shown in FIGS. 11 to 13 present a different configuration in terms of the contact plates 6, 9 and the dissipater units 15, which present transverse ribs 15*b* instead of axial ones.

Accordingly, it can be seen that the contact plates 6, 9 present respective extensions 6*a*, 9*a* of convex cross-section of the surfaces opposite to the surfaces in contact with the receiving unit 3. Each one of the free surfaces of these extensions 6*a*, 9*a* has the same dimensions as the first surfaces of the units of Peltier cells 5, 8 with which they are in contact. The convex cross-section of the extensions 6*a*, 9*a* permits a more uniform distribution of the heat energy evolved by the first sides of the units of Peltier cells 5, 8 in the interior of the contact plates 6, 9, thereby avoiding the formation of "foci" of heat energy in the surfaces in contact with the receiving unit 3.

In the device of the present invention, the units of Peltier cells 5, 8 that are used can be conventional in themselves. So, for the generation of heat energy for heating and/or cooling of physiological fluids to temperatures between 35° C. and 40° C. Peltier cells of 12 V and 3.50 A can be used with a capacity to generate temperatures between 5° C. and 80° C. Operating at half capacity, two such units of Peltier cells are sufficient for transferring enough heat energy for maintaining said temperatures of the physiological fluid via contact plates 6, 9 made of aluminum with a thickness of between 10 and 20 mm, a depth of 70 to 120 mm and a width of 180 to 250 mm.

The invention claimed is:

1. A device for adjusting the temperature of a physiological fluid, comprising
    a casing (1),
    a first heat energy generating unit (2),
    a heat energy receiving unit (3) inside which the fluid flows along a passage from a fluid inlet (3*a*) to a fluid outlet (3*b*) and which comprises a flat body (3*d*) having at least one first large surface (3*e*) made of a heat conductor material,
    a control unit (4) for controlling at least said first heat energy generating unit (2) and which includes a microprocessor (4*a*);
    characterized in that
    the first heat energy generating unit (2) includes a plurality of first units of Peltier cells (5) and at least one first contact plate (6) which is made of a heat conductor material and which is placed in contact with a second side (5*b*) of the units of Peltier cells (5),
    the receiving unit (3) is removably installed in the first generating unit (2) such that it is in contact with the first contact plate (6),
    the casing (1) comprises an access hatch (10) to the interior of the casing (1), facing said first heat energy generating unit (2), and a space (11) defined between said hatch (10) and said first generating unit (2) in which the removable receiving unit (3) is housed,
    the fluid inlet (3*a*) of the receiving unit (3) includes a first hollow connector (12*a*),
    the fluid outlet (3*b*) of the receiving unit (3) includes a second hollow connector (12*b*), said first and said second hollow connector (12a,12b) projecting from the surface of the receiving unit (3) opposite to said first large surface (3e), the hatch (10) presenting a first passage hole (13a) for the first connector (12a) and a second passage hole (13b) for the second connector (12b).

2. A device according to claim 1, characterized in that it further comprises a second heat energy generating unit (7) containing a plurality of second units of Peltier cells (8); at least one second contact plate (9) made of a heat conductor material placed in contact with a second side (8b) of the units of Peltier cells (8), said control unit (4) also controlling said second generating unit (7), the receiving unit (3) comprising a second large surface (3f) made of a heat conductor material, opposite to the first large surface (3e), and being arranged in contact with the first and second contact plate (6,9), the receiving unit (3) being removably installed between the first (2) and second heat energy generating unit (7).

3. A device according to claim 1, characterized in that it comprises at least one first temperature sensor (17) which detects the temperature in said first contact plate and which is connected to the control unit (4), and in that a microprocessor (4b) is programmed to supply electrical energy to said first units of Peltier cells (5) depending on the difference between a pre-established nominal temperature and the temperature detected by the temperature sensor (17).

4. A device according to claim 2, characterized in that it comprises at least one first temperature sensor (17) which detects the temperature in said first contact plate and which is connected to the control unit (4), and in that a microprocessor (4b) is programmed to supply electrical energy to said first units of Peltier cells (5) depending on the difference between a pre-established nominal temperature and the temperature detected by the temperature sensor (17).

5. A device according to claim 2, characterized in that it comprises at least one second temperature sensor (17) which detects the temperature in said second contact plate and which is connected to the control unit (4), and in that a microprocessor (4b) is programmed to supply electrical energy to said second units of Peltier cells (5) depending on the difference between a pre-established nominal temperature and the temperature detected by the temperature sensor (17).

6. A device according to claim 1, characterized in that the microprocessor (4b) is programmed to control the polarity of the electric current supplied to the units of Peltier cells (5,8) in order to heat up or cool down the second side (5b,8b) of the units of Peltier cells (5,8).

7. A device according to claim 2, characterized in that the microprocessor (4b) is programmed to control the polarity of the electric current supplied to the units of Peltier cells (5,8) in order to heat up or cool down the second side (5b,8b) of the units of Peltier cells (5,8).

8. A device according to claim 3, characterized in that the microprocessor (4b) is programmed to control the polarity of the electric current supplied to the units of Peltier cells (5,8) in order to heat up or cool down the second side (5b,8b) of the units of Peltier cells (5,8).

9. A device according to claim 4, characterized in that the microprocessor (4b) is programmed to control the polarity of the electric current supplied to the units of Peltier cells (5,8) in order to heat up or cool down the second side (5b,8b) of the units of Peltier cells (5,8).

10. A device according to claim 5, characterized in that the microprocessor (4b) is programmed to control the polarity of the electric current supplied to the units of Peltier cells (5,8) in order to heat up or cool down the second side (5b,8b) of the units of Peltier cells (5,8).

11. A device according to claim 1, characterized in that the first heat energy generating unit (2) is a heating unit, the second side (5b) of the first plurality of units of Peltier cells (5) that is in contact with the first contact plate (6) is the hot side of the first plurality of units of Peltier cells (5).

12. A device according to claim 2, characterized in that the first heat energy generating unit (2) is a heating unit, the second side (5b) of the first plurality of units of Peltier cells (5) that is in contact with the first contact plate (6) is the hot side of the first plurality of units of Peltier cells (5).

13. A device according to claim 3, characterized in that the first heat energy generating unit (2) is a heating unit, the second side (5b) of the first plurality of units of Peltier cells (5) that is in contact with the first contact plate (6) is the hot side of the first plurality of units of Peltier cells (5).

14. A device according to claim 1, characterized in that the first heat energy generating unit (2)) is a cooling unit, the second side (5b) of the first plurality of units of Peltier cells (5) that is in contact with the first contact plate (6) is the cold side of the first plurality of units of Peltier cells (5).

15. A device according to claim 2, characterized in that the first heat energy generating unit (2)) is a cooling unit, the second side (5b) of the first plurality of units of Peltier cells (5) that is in contact with the first contact plate (6) is the cold side of the first plurality of units of Peltier cells (5).

16. A device according to claim 4, characterized in that the first heat energy generating unit (2)) is a cooling unit, the second side (5b) of the first plurality of units of Peltier cells (5) that is in contact with the first contact plate (6) is the cold side of the first plurality of units of Peltier cells (5).

17. A device according to claim 2, characterized in that the second heat energy generating unit (7) is a heating unit, the second side (8b) of the second plurality of units of Peltier cells (8) that is in contact with the second contact plate (9) is the hot side of the second plurality of units of Peltier cells (8).

18. A device according to claim 1, characterized in that the second heat energy generating unit (7) is a cooling unit, the second side (8b) of the second plurality of units of Peltier cells (8) that is in contact with the second contact plate (9) is the cold side of the second plurality of units of Peltier cells (8).

19. A device according to claim 2, characterized in that the second heat energy generating unit (7) is a cooling unit, the second side (8b) of the second plurality of units of Peltier cells (8) that is in contact with the second contact plate (9) is the cold side of the second plurality of units of Peltier cells (8).

20. A device according to claim 1, characterized in that the passage (3c) of the receiving unit (3) comprises a coil between the inlet (3a) and the outlet of the fluid (3b).

21. A device according to claim 2, characterized in that the passage (3c) of the receiving unit (3) comprises a coil between the inlet (3a) and the outlet of the fluid (3b).

22. A device according to claim 1, characterized in that the casing (1) comprises a flat compartment (14) for housing the receiving unit (3), said compartment (14) including an access opening (14a) for the insertion of the receiving unit (3) and at least one wall of said compartment (3) consisting of said first contact plate (6); and the fluid inlet and outlet (3*a*,3*b*) of the receiving unit (3) are arranged on the same side of the receiving unit (3), in such a way that, when the receiving unit (3) is inserted in said compartment (14), the fluid inlet and outlet (3*a*,3*b*) are accessible via said access mouth (14*a*).

23. A device according to claim 2, characterized in that the casing (1) comprises a flat compartment (14) defined between said first (6) and said second contact plate (9) for housing the receiving unit (3), said compartment (14) including an access opening (14*a*) for the insertion of the receiving unit (3); and the fluid inlet and outlet (3*a*,3*b*) of the receiving unit (3) are arranged on the same side of the receiving unit (3), in such a way that, when the receiving unit (3) is inserted in the compartment (14), the fluid inlet and outlet (3*a*,3*b*) are accessible via said access opening (14*a*).

\* \* \* \* \*